United States Patent
Kohayakawa

[19]

[11] Patent Number: 6,131,574
[45] Date of Patent: *Oct. 17, 2000

[54] OPHTHALMOLOGICAL APPARATUS

[75] Inventor: Yoshimi Kohayakawa, Yokohama, Japan

[73] Assignee: Canon Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/889,758

[22] Filed: Jul. 10, 1997

Related U.S. Application Data

[63] Continuation of application No. 08/668,636, Jun. 21, 1996, abandoned, which is a continuation of application No. 08/403,118, Mar. 13, 1995, abandoned, which is a continuation of application No. 08/109,457, Aug. 20, 1993, abandoned, which is a continuation of application No. 07/680,932, Apr. 5, 1991, abandoned.

[30] Foreign Application Priority Data

Apr. 6, 1990 [JP] Japan ..................................... 2-91416

[51] Int. Cl.$^7$ ........................................................ A61B 3/16
[52] U.S. Cl. ............................. 128/645; 351/223; 351/208
[58] Field of Search ..................................... 128/645–648, 128/652; 351/208, 223

[56] References Cited

U.S. PATENT DOCUMENTS

| | | | |
|---|---|---|---|
| 4,253,743 | 3/1981 | Matsumura | 351/208 |
| 4,665,923 | 5/1987 | Kobayashi | 128/648 |

FOREIGN PATENT DOCUMENTS

| | | | |
|---|---|---|---|
| 61-276533 | 12/1986 | Japan . | |
| 2223107 | 3/1990 | United Kingdom | 128/646 |

*Primary Examiner*—Mickey Yu
*Assistant Examiner*—Tram A. Nguyen
*Attorney, Agent, or Firm*—Fitzpatrick, Cella, Harper & Scinto

[57] ABSTRACT

An ophthalmological apparatus includes a projecting system for projecting a light from an index light source emitting a visual ray onto an eye to be examined, and a reflecting optical system located so as to face to the eye to be examined and adapted to reproduce a corneal reflex image of the index light source as a mirror image.

13 Claims, 6 Drawing Sheets

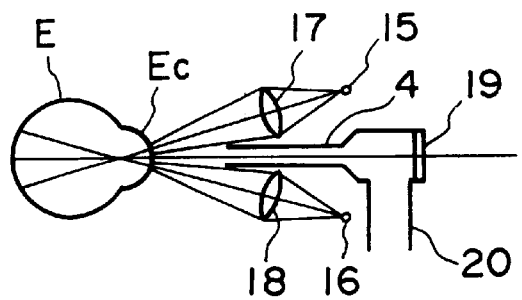
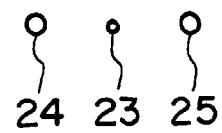
FIG. 5  FIG. 6
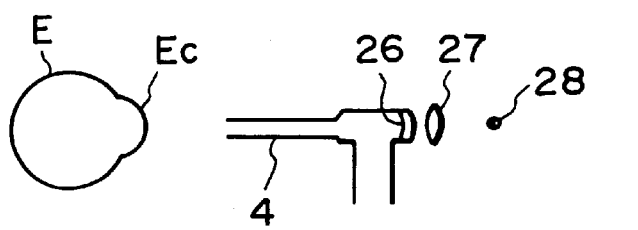
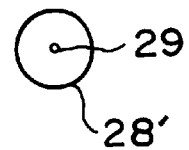
FIG. 7  FIG. 8
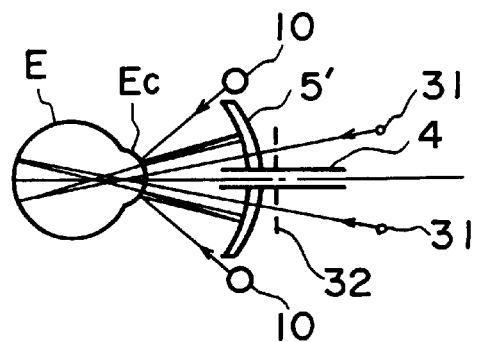
FIG. 9

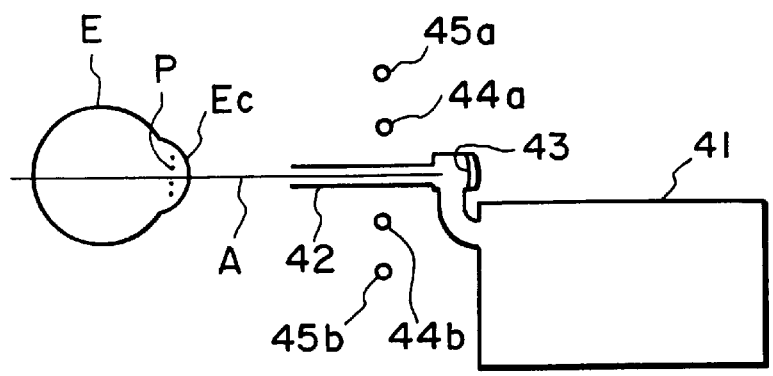
F I G. 10
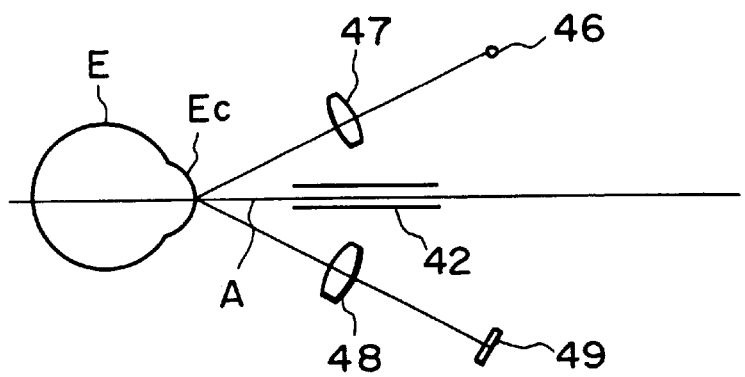
F I G. 11
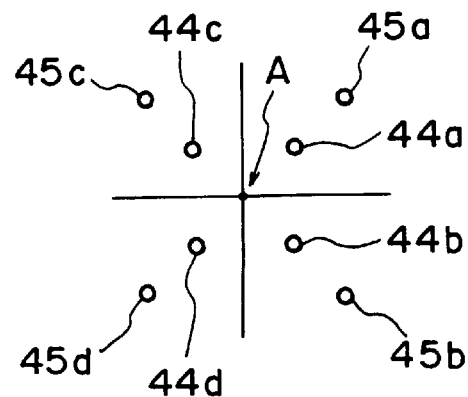
F I G. 12

OPHTHALMOLOGICAL APPARATUS

This application is a continuation of U.S. application Ser. No. 08/668,636, filed Jun. 21, 1996, now abandoned, which is a continuation of U.S. application Ser. No. 08/403,118, filed Mar. 13, 1995, abandoned, which is a continuation of U.S. application Ser. No. 08/109,457, filed Aug. 20, 1993, abandoned, and which is a continuation of U.S. application Ser. No. 07/680,932, filed Apr. 5, 1991, abandoned.

BACKGROUND OF THE INVENTION

1. Field of the Invention

The present invention relates an ophthalmological apparatus in which a subject can ascertain a positioning condition for his eye easily and correctly by himself.

2. Related Background Art

An ophthalmological apparatus is known, wherein a subject visually views the anterior part of his eye in order to position it, as disclosed in the Japanese Patent Laid-Open Application No. 61-276533.

SUMMARY OF THE INVENTION

An object of the present invention is to provide an improved ophthalmological apparatus wherein a subject can perform the positioning of his eye with a simple construction and an optometry opertation correctly by himself.

Another object of the present invention is to provide an ophthalmological apparatus wherein a subject can perform the fine positioning of his eye by observing the corneal reflex image of an index light source with the eye to be examined, and can also perform the rough positioning for the eye by using the anterior eye image.

Another object of the present invention is to an ophthalmological apparatus wherein a subject can easily perform the positioning for the eye to be examined by forming the corneal reflex image of the index light source on a central portion of the black pupil reflected in the visual field.

BRIEF DESCRIPTION OF THE DRAWINGS

FIG. 5 is a schematic view showing a third embodiment of the present invention;

FIG. 6 is a view showing luminous the flux viewed by an eye to be examined, in the third embodiment;

FIG. 7 is a schematic view showing a fourth embodiment of the present invention;

FIG. 8 is a view showing a luminous flux viewed by an eye to be examined, in the fourth embodiment;

FIG. 9 is a schematic view showing a fifth embodiment of the present invention;

FIG. 10 is an elevational constructural view of an ophthalmological apparatus according to a sixth embodiment of the present invention;

FIG. 11 is a schematic constructural view of the apparatus of FIG. 10;

FIG. 12 is a view showing an arrangement of light sources for visual rays;

DESCRIPTION OF THE PREFERRED EMBODIMENTS

Figure 1:
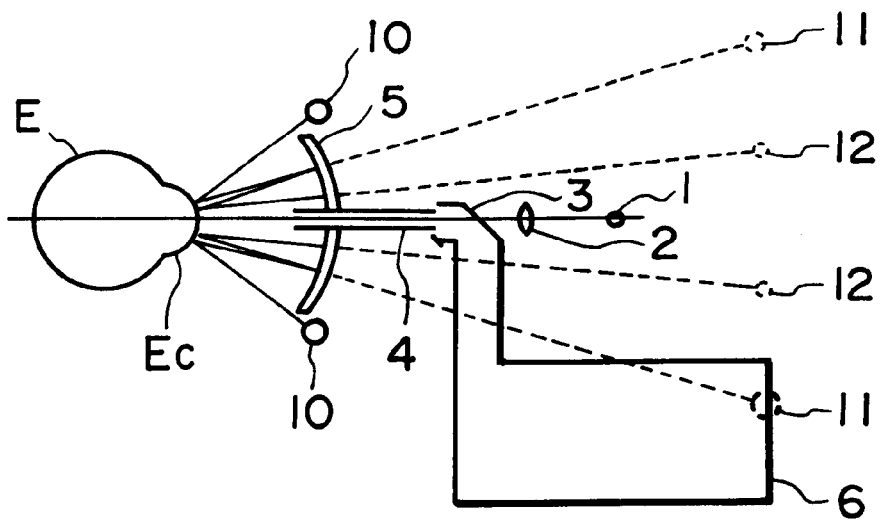
FIG. 1 is a schematic view showing a first embodiment of the present invention.

FIG. 1 shows a first embodiment of an ophthalmological apparatus according to the present invention. Light beams from light sources (index light sources) 10 for emitting visual rays are reflected at a cornea Ec reach to a concave mirror 5 to form virtual images (first mirror images) 11. The light beams reflected by the mirror 5 are reflected again at the cornea Ec to reach to the concave mirror 5 to form virtual images (second mirror images) 12. On the other hand, a light beam from a light source (reference light source) 1 for emitting visual rays passes through a lens 2, a window 3 and a nozzle 4 and is projected onto an eye E to be examined. The nozzle 4 is connected to an air flow generating device 6 such as a piston or a pump. When the positioning for the eye is finished, the air flow is automatically generated by a conventional method for photo-detecting the corneal reflex light, thus deforming the cornea Ec. The deformed condition of the cornea is detected by means of a conventional optical method, whereby the intraocular pressure is mesured from the relation between the intensity of the air flow and the deformed condition.

Figure 2A:
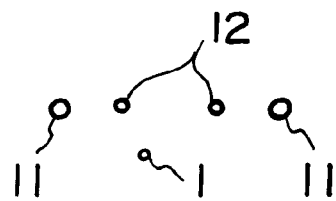
FIGS. 2A, 2B and 2C are views showing the luminous flux (bundles of light beams) viewed at by an eye to be examined, in the first embodiment.
Figure 2B:
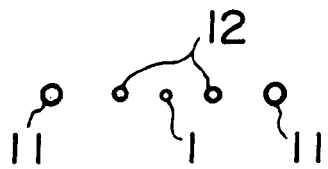
Figure 2C:
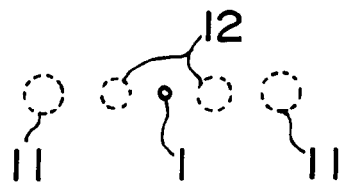

FIGS. 2A to 2C show luminous light (bundles of light beams) which are visually ascertained by an subject. Particularly, FIG. 2A illustrates a condition when the alignment with relation to an axis of the air is improper, and FIG. 2B illustrates a condition when the positioning is finished three-dimensionally. FIG. 2C illustrates a condition when the positioning is improper in an air flow direction; in this case, the mirror images 11, 12 become dim. Incidentally, since the positions of the mirror images 11, 12 with relation to a direction of the optical axis vary in accordance with the curvature of the mirror 5, such curvature may be selected so that the mirror images are formed at a distance of distinct vision.

Figure 3:
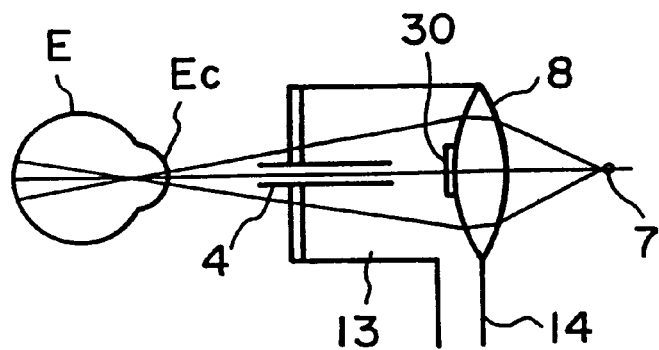
FIG. 3 is a schematic view showing a second embodiment of the present invention.
Figure 4A:
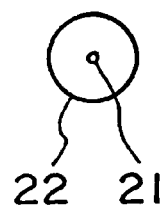
FIGS. 4A, 4B and 4C are views showing the luminous flux viewed at by an eye to be examined, in the second embodiment.
Figure 4B:
Figure 4C:
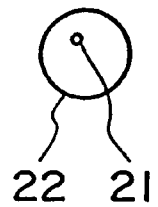

Next, FIG. 3 shows a second embodiment according to the present invention. A light beam from a light source 7 for emitting visual rays is condensed by a lens 8 at a position spaced away from a vertex of the cornea by half of the radius of curvature of the cornea. A part of the light beam is reflected at the cornea Ec and then passes through the nozzle 4 to reach to a mirror 30, where the light beam is reflected. The reflected light beam passes through the nozzle 4 again to reach to the eye E to be examined. FIGS. 4A to 4C show the luminous light which are visually ascertained by the eye E to be examined. Ring-shaped light 22 is a light which is directly incident on the eye E to be examined without being reflected by the cornea and the mirror. Luminous light 21 is a bundle of light which is reflected by the cornea Ec and the mirror 30. The luminous light 21 is sensitive to eccentricity, and easily becomes dim when the distance in the direction of the optical axis is changed.

In the present embodiment, the light source 7 serves as both the index light source and the reference light source. FIG. 4A illustrates a condition when the positioning is proper, FIG. 4B illustrates a condition when the luminous light 21 is out of position in the direction of the optical axis, and FIG. 4C illustrates a condition when the luminous light is eccentric. A chamber 13 is connected to the air flow generating device at a location 14.

FIG. 5 shows a third embodiment according to the present invention. Light beams from light sources 15, 16 for emitting visual rays are condensed within the eye by lenses 17, 18, respectively, at a position spaced away from the vertex of the cornea Ec by half of the radius of curvature of the cornea. Parts of the light beams are reflected at the cornea Ec and then pass through the nozzle 4 to reach to a mirror 19 disposed rearwardly of the nozzle 4, where the light beams are reflected. The reflected light beams pass through the nozzle 4 again to reach to the eye E to be examined. FIG. 6 shows the light beams which are visually ascertained by the eye to be examined, when the registering is proper. Light beams 24, 25 are ones directly incident on the eye to be examined, and a light beam 23 is one reflected by the cornea Ec and the mirror 19. Since the light beam 23 is sensitive to minor eccentricity, and easily becomes dim when there is any error in distance in the direction of the optical axis, it is possible to perform the positioning for the eye correctly. A part 20 is connected to the air flow generating device.

Also, in this embodiment, the light sources 15, 16 serve as both index light source and the reference light source.

FIG. 7 shows a fourth embodiment according to the present invention. A small ring-shaped light source 28 for emitting visual rays is located at a focal position of a lens 27. A concave mirror 26 partially transmits a light beam, so the light beam from the light source 28 is incident on the eye E to be examined. A part of the light beam is reflected at the cornea Ec to reach to the concave mirror 26, where the light beam is reflected again. The reflected light beam is incident on the eye again through the nozzle 4. The concave mirror 26 serves to enlarge the light beam. FIG. 8 shows the luminous light which is visually ascertained by the eye to be examined. Ring-shaped luminous light 28' is seen and luminous light 29 is also seen at a center of the ring-shaped luminous light 28', the luminous light 29 being incident on the eye to be examined after reflected by the cornea and the mirror 26 through the nozzle 4. The positioning for the eye can be performed so that the luminous light 29 is positioned at the center of the ring-shaped luminous light 28'.

Next, a fifth embodiment according to the present invention is shown in FIG. 9. Light sources 10 for emitting the visual rays and a mirror 5' are the same as those used in the first embodiment shown in FIG. 1. However, unlike the embodiment of FIG. 1, in this fifth embodiment, light beams from light sources 31 for emitting the visual rays are directly incident on the eye through a diaphragm 32 having two holes. In this case, the mirror 5' partially transmits the light beam.

Although the luminous light visually ascertained by the subject is similar to that shown in FIGS. 2A to 2C, in this embodiment, in place of the direct central light beam 1, direct light beams from the light sources 31 will be seen in the proximity of the light beams 12.

As mentioned above, according to the aforementioned embodiments, since, unlike the direct light beam, the reflected light beam reflected by the cornea and the mirror is sensitive to being shifted and easily becomes dim with respect to the position of the eye to be examined, the registering can be effected with high accuracy by positioning the reflected light beam or beams with the direct light beam.

FIG. 10 is an elevational view of an ophthalmological apparatus of a sixth embodiment according to the present invention, FIG. 11 is a plan view of the apparatus, and FIG. 12 shows an arrangement of light sources for visual rays looked at from a subject's side. A concave mirror 43 is provided behind a nozzle 42 for injecting an air stream from an compressed air generating device 41 toward the eye E to be examined. Around the nozzle 42, four light sources 44a to 44d for visual rays are located symmetrically with respect to a direction A of the air stream, and four light sources 45a to 45d are similarly located outside the light sources 44a to 44d. A measuring light source 46 and a lens 47 are located in front of and above the cornea Ec, and a photo-sensor 49 and a lens 48 are located symmetrically with the above elements 46, 47, respectively, with respect to the air stream direction A.

The light sources 44a to 44d and 45a to 45d for visual rays serve to emit the visual light beams to the cornea Ec of the eye E to be examined obliquely with respect to the air stream direction A, thus forming a reflected image P on the cornea Ec. As the eye E to be examined moves, the reflected image P moves accordingly. The subject can perform alignment by observing the reflected image P reflected by the concave mirror 43 while moving his eye to be examined. Since the concave mirror can enlarge the image, the concave mirror is convenient for the positioning with high accuracy. It is possible to obtain the same technical advantage by using the combination of a convex lens and a convex mirror.

When the alignment is completed, the air stream from the compressed air generating device 41 is injected onto the cornea Ec through the nozzle 42, thus deforming the cornea Ec with the pressure. The deformation of the cornea Ec is detected by a cornea deformation detecting system shown in FIG. 11. That is, the light beam from the measuring light source 46 is projected on the cornea Ec through the lens 47, and the reflected light at the cornea Ec is received by the photo-sensor 49 through the lens 48. By detecting the amount of deformation of the cornea Ec on the basis of a signal from the photo-sensor 49, a value of the intraocular pressure can be measured from the pressure at that time.

Incidentally, in the above-mentioned conventional case, the black pupil was merely seen in the visual field of the subject. However, in the illustrated embodiment, since the reflected images can be seen in the vicinity of the center of the visual field, the position of the center of the visual field can more easily be determined, and, therefore, the alignment can be effected by determining the discrepancy in the reflected images. In case it is difficult to determine the operating distance correctly due to the relative wide range of the reflected images, the eye E to be examined is slightly moved in a forward or rearward direction after the reflected images are positioned in the axial direction. The images are positioned on the basis of the output from the photo-sensor 49 and then the air stream is automatically emitted from the nozzle 42, thus performing the measurement.

Figures 13, 14:
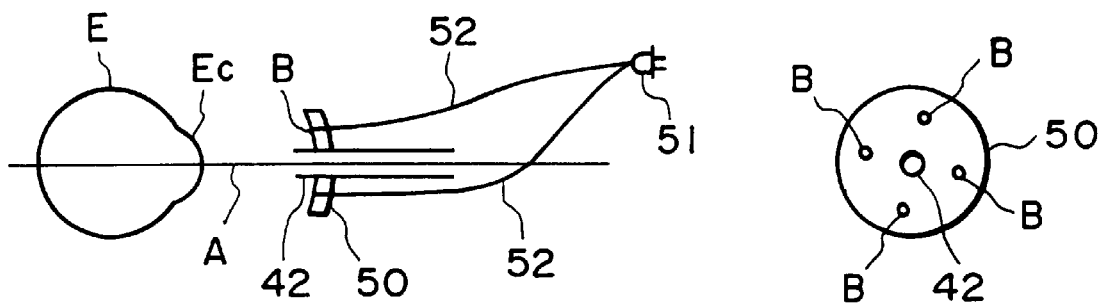
FIG. 13 is a schematic view showing a seventh embodiment of the present invention.
FIG. 14 is a plan view of a concave mirror looked at from a side of an eye to be examined.

FIG. 13 shows a seventh embodiment according to the present invention, where a concave mirror 50 is provided around the nozzle 42. Leading ends of fibers 52 for guiding the light from a light source 51 are embedded in the concave mirror 50. FIG. 14 shows the concave mirror 50 looked at from a side of the eye E to be examined. As seen from FIG. 14, the leading ends B of the fibers 52 are located symmetrically with respect to the center of the nozzle 42.

In the present embodiment, due to the presence of the nozzle 42, the corneal reflex image cannot be seen when the alignment is proper, but can be seen when the alignment is improper. Further, since the concave mirror 50 is positioned near the eye to be examined to provide a great magnifying power, the image of the eye E to be examined is observed at a given position on the optical axis; however, because the image becomes dim when the image is shifted from the given position, it is possible to determine the operating distance relatively correctly.

When the radius of curvature of the concave mirror 50 is twice of a distance between the cornea Ec and the concave mirror 50, the cornea Ec of the eye E to be examined will be positioned at the focal position, and therefore, it is possible to project the image of the eye E to be examined at a great distance with great magnification.

Figure 15:
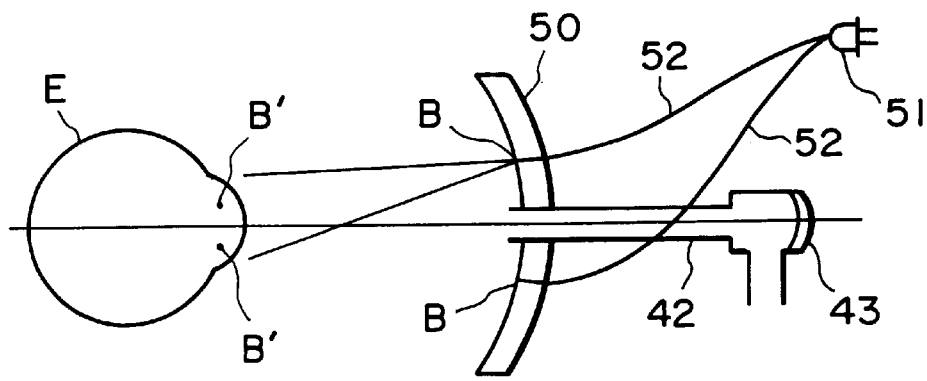
FIG. 15 is a schematic view showing an eighth embodiment of the present invention.

FIG. 15 shows an eighth embodiment according to the present invention. In this embodiment, both the concave mirror 43 used in the embodiment of FIG. 10 and the concave mirror 50 used in the embodiment of FIG. 13 are used. Also are similarly used the light source 51 for visual rays associated with the concave mirror 50 and the fibers 52 for guiding the light from the light source.

Figure 16:
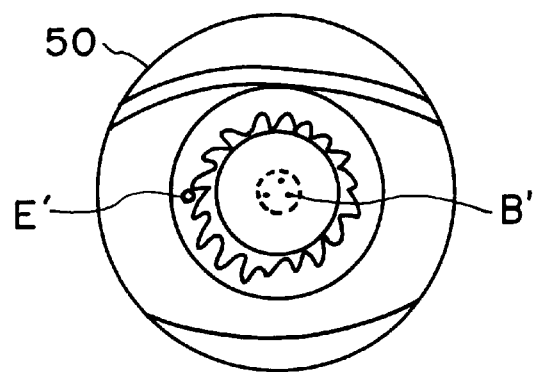
FIG. 16 is a plan view of a concave mirror looked at from a side of an eye to be examined.

FIG. 16 shows the visual field of the subject in the eighth embodiment. In this visual field are projected the image E' of the anterior eye magnified by the concave mirror 50 and the corneal reflex image B' formed by the concave mirror 43 located behind the nozzle 42. Since the image E' of the anterior eye easily becomes dim or out of position due to the great magnifying power of the image, it is possible to determine the position of the image in a position where the image can be seen distinctly. Further, by registering the projected pupil with the corneal reflex image B' without any eccentricity, the vertical position against the optical axis can be determined.

In the aforementioned embodiments, while an example that the light sources 44a to 44d and 45a to 45d each emits the spot-like light was explained, these light sources may be constituted so as to emit ring-shaped light beams. Light sources located successively in a radial direction with respect to the air stream direction A may be utilized. In this case, in the embodiment as shown in FIG. 10, it is possible for the subject to determine the distance in the air stream direction A by the extent to which the light source can be seen and to determine the vertical distance on the basis of the symmetry of the light sources.

The above-mentioned ophthalmological apparatus is particularly useful for applying to, for example, a home use noncontact tonometer or the like, because the subject can easily position his or her eye at a predetermined operating distance from the ophthalmological apparatus by oneself.

However, the distance between the cornea of the eye and a curved mirror is dependent on the diopter of the eye, i.e. at the diopter the eye sees the reflected image of the index light source clearly.

Therefore, embodiments which will be described hereinafter relate to an ophthalmological apparatus which is embodied in consideration of the aforementioned embodiments, and which can eliminate measuring error occurs by the change in the operating distance due to the variation in the diameter of the subject's eye, by adding the previous positioning of an optical alignment member with the subject's diopter when the subject performs the alignment by himself.

Figure 17:
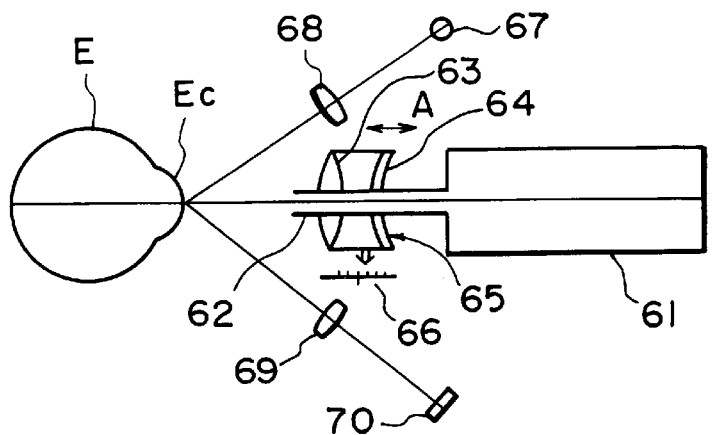
FIG. 17 is a schematic view showing an optical arrangement according to a ninth embodiment of the present invention.

FIG. 17 shows a ninth embodiment according to the present invention. According to this embodiment, the ophthalmological apparatus comprises a body casing 61 including a compressed air generating device, a nozzle 62 for injecting the air stream generated by the compressed air generating device toward the cornea Ec of the eye E to be examined, and an optical alignment member 65 comprising a lens 63 and a convex mirror 64 and arranged around the nozzle 62. The subject can perform the alignment by seeing the image of his or her eye E by the optical alignment member 65. Both the lens 63 and the convex mirror 64 for constituting the optical alignment member 65 are constructed as one body, or at least one of these elements 63, 64 can be shifted in the air stream direction A. Thus, by setting the position of the optical alignment member 65 by a scale board 66 with scales of diopter value, the diopter of the eye E to be examined can be adjusted. On the other hand, a light beam emitted from a light source 67 is projected onto the eye E through a lens 68, and a light beam reflected at the cornea Ec is directed to a photo-sensor 70 through a lens 69. In this way, mentioned above, the intraocular tension is measured by detecting the deformation of the cornea Ec due to the injection of the air stream.

Figure 18:
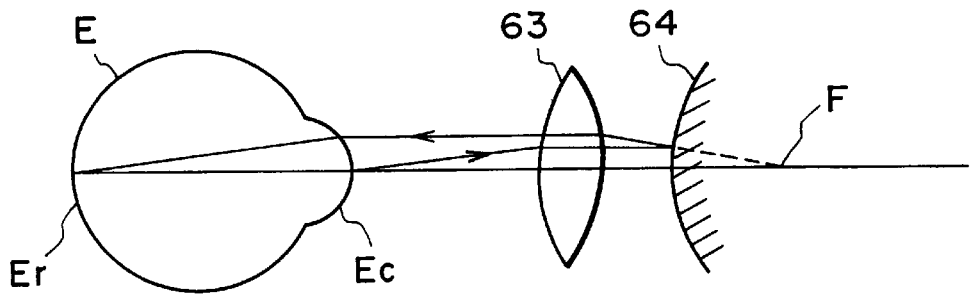
FIG. 18 is a view showing an optical relation between optical alignment members.

FIG. 18 shows an optical arrangement of the optical alignment member 65. In this arrangement, the light reflected at the cornea Ec is collimated by the lens 63 and is reflected by the convex mirror 64, and the reflected light is again collimated by the lens 63 to reach to the eye, where the image is formed on an eye fundus Er. A point F designates the foci of the lens 63 and the convex mirror 64. Prior to the measurement, the subject previously adjusts the position of the optical alignment member 65 to his diopter by utilizing the scale board 66. During the measurement, the subject positions his eye E to be examined in a position spaced away from the nozzle 62 by a given distance, by moving his eye E slightly in the forward or rearward direction. At this position, the subject can visually ascertain the image of his eye distinctly. Since the image becomes dim in a position other than this position, it is possible to register the eye E to be examined with a given operating distance of the apparatus.

Figure 19:
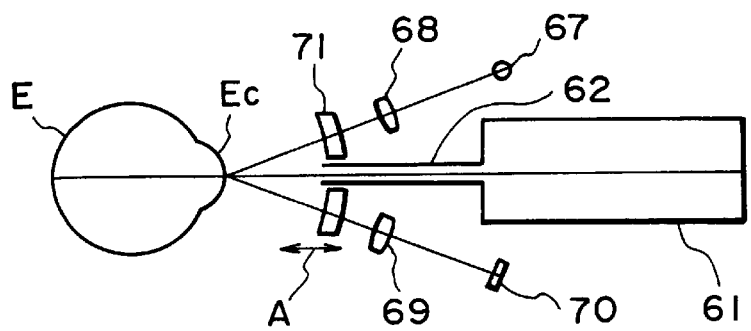
FIG. 19 is a schematic view showing an optical arrangement according to a tenth embodiment of the present invention.

FIG. 19 shows a tenth embodiment according to the present invention. In this embodiment, a concave mirror 71 is provided as an optical alignment member in place of the lens 63 and the convex mirror 64 shown in FIG. 17. The subject can perform alignment by projecting his eye E onto this concave mirror 71. In this case, the concave mirror 71 comprises a dichroic mirror for prohibiting the passage of the visual ray but for permitting the passage of the near infrared ray emitted from a light source 67.

Accordingly, by projecting the light beam emitted from the light source 67 onto the eye E to be examined through a lens 68 and the concave mirror 71 and by sending the light beam reflected at the cornea Ec to a photo-sensor 70 through the concave mirror 71 and a lens 69, the deformation of the cornea Ec can be detected, and thus, the intraocular pressure value can be obtained. Also in this case, the position of the concave mirror 71 is adjusted to the subject's diopter using the scale board 66 and the position of the concave mirror 71 is set by moving it in the direction A. When the eye E to be examined is positioned in a position spaced away from the apparatus by a given distance, the subject can visually ascertain the image of his eye E distinctly in that position.

Since the image becomes dim in a position other than this position, it is possible to register the eye E to be examined with a given operating distance of the apparatus.

Figure 20:
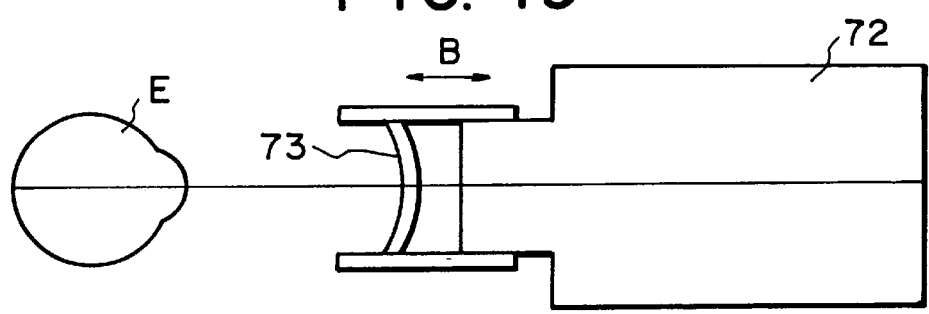
FIG. 20 is a schematic view showing an optical arrangement according to an eleventh embodiment of the present invention.

FIG. 20 shows an eleventh embodiment according to the present invention. In this embodiment, the ophthalmological apparatus is applied to a refractometer. A concave mirror 73 attached to a front part of a measuring system 72 can be automatically shifted in a direction B along the optical axis by an output from a control system. Preferably, the concave mirror 73 permits the passage of the near infrared ray and prohibits the passage of the visual ray. However, this mirror may comprise a concave half-mirror.

During the measurement, the eye E to be examined faces the concave mirror 73 so that the refractivity of the eye can be measured by the measuring system 72. The diopter of the eye E to be examined can be obtained by this measurement. The concave mirror 73 is shifted and adjusted in the direction of the optical axis by the control system in accordance with the diopter. In this condition, the subject performs the measurement of the refractivity of the eye again by using the proper operating distance at which the image of the eye to be examined is seen distinctly by projecting his eye E onto the concave mirror 73.

In this way, since the position of the concave mirror 73 can be adjusted each time after the refractivity of the eye has been roughly measured, the subject can determine the operating distance correctly, and the value of the refractivity of the eye can be measured with high accuracy by the re-measurement.

Although the optical alignment member include a mirror surface, it should be noted that various modifications other than the illustrated ones can be adopted. When the optical alignment member consists of the mirror surface and the lens system, in place of the fact that the diopter is adjusted by shifting the mirror surface in the direction of the optical axis, at least a part of the lens system may be shifted to adjust the diopter.

According to the embodiments mentioned above, since the eye to be examined can be positioned with the given operating distance regardless of the diopter of the subject's eye to be examined, it is possible to reduce the measurement error due to the difference in the diopter.

What is claimed is:

1. A kit for an eye examining apparatus comprising:
    reflecting optical means for facing an eye to be examined and for focusing an image of an anterior part of the eye to be examined onto a fundus of the eye to be examined;
    positioning light sources for producing visual rays, said positioning light sources being located symmetrically with respect to an optical axis of said reflecting optical means, wherein said reflecting optical means comprises means for focusing light beams from said positioning light sources, reflected by a cornea of the eye to be examined, onto the eye fundus; and
    a positioning reference light source adapted to be positioned in front of the eye to be examined for confirming positional alignment of said apparatus with the eye to be examined of the examinee by comparing the position of said positioning reference light source with light beams from said positioning light sources focused onto the eye fundus by said reflecting optical means.

2. A kit according to claim 1, wherein said reflecting optical means has an opening on the optical axis thereof comprising means for transmitting a light beam from the positioning reference light source to the eye fundus of the eye to be examined, and includes means for focusing the light beams from said positioning light sources onto the eye fundus without substantially being influenced by the opening.

3. A kit according to claim 1, wherein said reflecting optical means comprises a concave mirror.

4. A kit for an eye examining apparatus comprising:
    projecting means for projecting a visual ray emitted from at least an index light source onto an eye to be examined;
    reflecting optical means for facing the eye to be examined and for reproducing a cornea reflected image of the index light source as a mirror image to be observed by the eye to be examined; and
    positioning reference light source means for facing the eye to be examined and for providing a positioning reference light source to confirm positional alignment of said apparatus with the eye to be examined of the examinee by comparing the position of said positioning reference light source means with the mirror image of the cornea reflected image of the index light source obtained by said reflecting optical means.

5. A kit according to claim 4, wherein said reflecting optical means comprises a concave mirror.

6. A kit for an eye examining apparatus comprising:
    projecting means for projecting a visual ray emitted from an index light source onto an eye to be examined;
    reflecting optical means for facing the eye to be examined and for reproducing a cornea reflected image of the index light source as a mirror image to be observed by the eye to be examined; and
    reference light source means for facing the eye to be examined and for emitting a visual ray which can be compared with the mirror image by an examinee whose eye is to be examined so that a registering condition is visually ascertained by the examinee whose eye is to be examined.

7. A kit according to claim 6, wherein said reflecting optical means comprises a concave mirror, and a nozzle for injecting an air stream for measuring the intraocular pressure of the eye to be examined, said nozzle passing through said concave mirror or being located at the rear of said concave mirror.

8. A kit apparatus according to claim 7, wherein a light path extending from said reference light source means or said mirror image to said eye to be examined passes through said nozzle.

9. A kit for a tonometer for measuring a value of an intraocular pressure of an eye to be examined, comprising:
    intraocular pressure detecting means for detecting the intraocular pressure by deforming a cornea of the eye to be examined of an examinee by ejecting an air stream from a nozzle to the cornea and detecting the deformation of the cornea photo-electrically;
    visual ray light sources for projecting visual rays onto the cornea from oblique directions symmetrical with respect to a direction of travel of the air stream;
    reflecting optical means for facing the cornea, for receiving the visual rays of said visual ray light sources reflected by the cornea, and for reflecting the visual rays reflected by the cornea whereby the examinee can perform an alignment operation to align said tonometer with the eye to be examined of the examinee while observing reflected images of said visual ray light sources of said tonometer, the images being reflected at the cornea and secondly at said reflecting optical means; and reference visual ray light source means for facing the eye to be examined and for providing a reference visual ray light whereby the examinee can perform the alignment operation by comparing the position of said reference visual ray light with the reflected images.

10. A kit according to claim 9, wherein an image of the reference visual ray light source means is adapted to be focused on an eye fundus of the eye to be examined through said nozzle, and the light beam from said visual ray light sources are adapted to be focused on the eye fundus of the eye to be examined by the reflection at the cornea of the eye to be examined and by the reflection by said reflecting optical means without being substantially influenced by said nozzle.

11. A kit according to claim 9, wherein said reflecting optical means is adapted to be shifted in a direction of an optical axis of said tonometer in accordance with a diopter of the eye to be examined.

12. A method for aligning an eye to be examined with an eye examining apparatus comprising the steps of:

forming, with the eye examining apparatus, a mirror image of an anterior part of the eye to be examined at a position so that the mirror image is observable by the eye to be examined;

emitting a visual ray from a light source of the eye examining apparatus so that the visual ray is observable by the eye to be examined at the same time as the mirror image; and aligning the eye to be examined with the eye examining apparatus by the examinee using the positional relationship between the mirror image and the visual ray both of which are viewed by the examinee at the same time.

13. A kit for an eye examining apparatus comprising:

index light source for projecting a visual ray onto an eye to be examined;

reflecting optical means for facing the eye to be examined and for reproducing a cornea reflected image of the index light source as a mirror image to be observed by the eye to be examined; and positioning reference light source means for facing the eye to be examined and for providing a positioning reference light source to confirm positional alignment of said apparatus with the eye to be examined of the examinee by comparing the position of said positioning reference light source means with the mirror image of the cornea reflected image of the index light source obtained by said reflecting optical means.

* * * * *

UNITED STATES PATENT AND TRADEMARK OFFICE
CERTIFICATE OF CORRECTION

PATENT NO.   : 6,131,574
DATED        : October 17, 2000
INVENTOR(S)  : Yoshimi Kohayakawa It is certified that error appears in the above-identified patent and that said Letters Patent is hereby corrected as shown below:

Title page,
Abstract:
Line 4, "to" ($2^{nd}$ occurrence) should be deleted.

Column 1:
Line 27, "opertation" should read -- operation --.
Line 34, "to" should read -- to provide --.
Line 44, "at" should be deleted.
Line 50, "at" should be deleted.
Line 54, "luminous the" should read -- the luminous --.
Line 62, "constructural" should read -- constructional --.
Line 66, "constructural" should read -- constructional --.

Column 2:
Line 29, "reach to" should read -- to reach --.
Line 47, "an" should read -- a --.
Line 49, "air" should read -- air flow --.

Column 3:
Line 52, "after" should read -- after being --.

Column 4:
Line 17, "an" should read -- a --.

Column 5:
Line 18, "of" should be deleted.
Line 27, "are similarly used" should be deleted.
Line 29, "source." should read -- source are similarly used. --.
Line 67, "occurs" should read -- that occurs --.

Column 6:
Line 1, "diameter" should read -- diopter --.
Line 24, "mentioned" should read -- as mentioned --.

UNITED STATES PATENT AND TRADEMARK OFFICE
CERTIFICATE OF CORRECTION

PATENT NO. : 6,131,574
DATED : October 17, 2000
INVENTOR(S) : Yoshimi Kohayakawa It is certified that error appears in the above-identified patent and that said Letters Patent is hereby corrected as shown below:

Column 7:
Line 30, "include" should read -- includes --.

Column 8:
Line 44, "apparatus" should be deleted.

Signed and Sealed this

Twenty-seventh Day of November, 2001

Attest:

NICHOLAS P. GODICI
*Attesting Officer*   *Acting Director of the United States Patent and Trademark Office*